United States Patent [19]

Dickert et al.

[11] Patent Number: 5,200,633
[45] Date of Patent: * Apr. 6, 1993

[54] SENSOR MATERIAL FOR MEASURING THE PARTIAL PRESSURE OF GASES OR VAPORS; AND GAS SENSORS

[75] Inventors: Franz Dickert, Nuremberg; Doris Zeltner, Erlangen; Gert Mages, Hemhofen; Heinz Kimmel, Buckenhof, all of Fed. Rep. of Germany

[73] Assignee: Siemens Aktiengesellschaft, Munich, Fed. Rep. of Germany

[*] Notice: The portion of the term of this patent subsequent to May 15, 2007 has been disclaimed.

[21] Appl. No.: 323,345

[22] Filed: Mar. 14, 1989

[30] Foreign Application Priority Data

Mar. 14, 1988 [DE] Fed. Rep. of Germany ....... 3808467
Mar. 14, 1988 [DE] Fed. Rep. of Germany ....... 3808468

[51] Int. Cl.$^5$ ..................... H01L 29/66; H01L 29/96
[52] U.S. Cl. ..................... 257/253; 257/40; 257/414
[58] Field of Search ............... 357/25, 8, 4, 1; 338/36, 34; 73/23, 29

[56] References Cited

U.S. PATENT DOCUMENTS 4,352,726 10/1982 Sugano et al. ..................... 204/195
4,579,751 4/1986 Forster .............................. 427/54.1
4,722,905 2/1988 Honeybourne et al. ............. 436/151
4,752,447 6/1988 Kimmel et al. ..................... 422/56
4,871,680 10/1989 Barraud et al. .................... 436/103
4,926,156 5/1990 Dickert et al. ..................... 338/36

FOREIGN PATENT DOCUMENTS 3217883 11/1983 Fed. Rep. of Germany .
3506686 8/1986 Fed. Rep. of Germany .
2947050 12/1986 Fed. Rep. of Germany .
3526348 2/1987 Fed. Rep. of Germany .
1429848 3/1976 United Kingdom .

OTHER PUBLICATIONS

"Sensorik", Springer Publishers, Heidelberg, 1986, pp. 166-170.

Primary Examiner—Andrew J. James
Assistant Examiner—Sara W. Crane
Attorney, Agent, or Firm—Kenyon & Kenyon

[57] ABSTRACT

A sensor material for gases or vapors including solvent vapors, comprising at least one hydrophobic metal complex with an ion mobility or ionic concentration or optical properties, which change under the effect of the gas or vapor. These metal complexes can be applied to suitable electrode arrangements or carriers and, in conjunction with simple measuring bridges or photometers, form a sensor system for gases and vapors.

32 Claims, 3 Drawing Sheets

SENSOR MATERIAL FOR MEASURING THE PARTIAL PRESSURE OF GASES OR VAPORS; AND GAS SENSORS

FIELD OF THE INVENTION

The present invention relates to a sensor material for measuring the partial pressure of gasses or vapors, especially solvent vapors. More particularly, the present invention relates to a sensor material which has electrical or optical properties that change under the effect of gasses or vapors, and to a gas or vapor sensor made of this material.

BACKGROUND OF THE INVENTION

Generally known sensors for measuring gases and vapors are optical filters containing a sensor material which reversibly changes color in the presence of a gas or vapor. This color change affects the transmittancy of the filter under the influence of the gases or vapors. These filters contain a mixture of an alkaline, or acid, color former, also known as a colorant, and a complementary compound. Triphenylmethane compositions, preferably crystal violet lactone, for example, can be utilized as color formers ("colorants"). These filters may also consist of colorants of the triphenylmethane system, preferably phthalein or sulphophthalein, which can be embedded in a matrix and provided with a carrier. The change in the transmittancy of the filter, under the effect of the gases or vapors, is converted into an electric signal and processed electronically. A filter such as generally described above is discussed in German Published Patent Application No. 35 06 686.

Metal complexes having ligands with hydrophobing properties are generally known. Examples of these metal complexes include: monodentate ligands, for example dimethyl formamide; bidentate ligands; chelate ligands, for example ethylenediamine and acetylacetone, podandens and macrocylenes such as crown ethers and cryptands.

A change in the electrical properties, for example a change in the dielectric constant or the electrical conductivity of a material can be utilized to measure, or sense, gases or vapors. For example, *Sensorik*, Springer Publishers, Heidelberg, 1986, pages 166–170 discusses the use of an ionic conductor as a sensor for oxygen or other gases. The ionic conductor separates two gas compartments, with different partial oxygen pressures, from each other. Porous platinum is applied to both sides of the ionic conductor and combines with the gas to be measured to form an electrode. If a difference exists between the gas pressures on the two sides of the ionic conductor, then a potential difference develops between the platinum electrodes which have formed on each side of the ionic conductor. This change in the electrical properties, as a result of the effect of the gas, can be used as a measured quantity to sense measure or sense gas or vapors.

Sensors, utilized to selectively determine components in a liquid or gaseous phase, having an MOS (metal oxide semiconductor) structure, such as a field-effect transistor or an MOS diode, are discussed in German Published Patent Application No. 35 36 348. These sensors are well suited to qualitatively or quantitatively determine analytes, for example molecules or ions, in liquid or gases. In these sensors a semi-conductive duct develops between a drain and a source electrode which are formed by the doped surface areas of the semi-conductor substrate. In the area of this duct, the substrate is covered by an insulating layer of silicon dioxide $SiO_2$. The silicon dioxide layer may additionally be covered by a thin protective layer of silicon nitride $Si_3N_4$. An additional gate insulating layer serves as a sensor layer for the gases to be measured and is arranged under a gate electrode, which is permeable to gas. This sensor layer with a thickness of approximately 0.01 to 1 $\mu$m consists of heteropolysiloxane. Heteropolysiloxanes are silicates which are organically modified by incorporating functional groups and, through reactions with other equally hydrolyzable and condensable metal compounds. By incorporating functional groups, for example primary amino groups, absorption centers develop which enable the desired selective interaction with analytes. As a result of the change in the electrical properties of the sensor layer and, possibly, of the change in the work function of the gate metal, as an additional influence quantity, the threshold voltage of the field-effect transistor and, therewith, the drain current, in the case of constant drain-source voltage, are changes, so that a quantitative determination of the gas is possible.

In a form of this sensor discussed in present German Published Patent Application 29 47 050, the gate electrode can be made of a very thin metal layer. This metal layer has islands which developed during its formation, which have not yet fully grown together. Apertures still remain between the islands, which enable the gas to pass through. In addition, the gate electrode can be made of a metal layer, which is provided with a pattern of bore holes of very small diameter, created, for example, by a laser ray, or by an electron or ion beam. Furthermore, the gate electrode can be designed as a grid electrode, or also be made of strips, arranged at a slight distance from each other.

The present invention provides an improved sensor for gases or vapors, which has an especially simple design and is provided with a sensitive sensor material.

SUMMARY OF THE INVENTION

According to the present invention, a sensor material comprises at least one hydrophobic metal complex. The invention is based on the realization that there are metal complexes with hydrophobing ligands, which, especially in thin films, under the effect of gases or vapors, can change their ionic concentration, their ion mobility and/or their transmittancy and, therewith, their dielectric or optical properties. The gas or solvent vapor in question can be quantitatively determined with resistance, capacitance or optical measurements.

These sensors permit the partial pressure or the concentration of gases and vapors of virtually all solvents to be measured using a simple method, even at room or ambient temperature. These solvents include aliphatic solvents, aromatic solvents, halogenated hydrocarbons, including alcohols and other protic solvents, and polar and aprotic solvents, such as, for example, acetone and dimethylformamide. Gases, such as ammonia, for example, can also be easily measured. The sensor material of the present invention attains a reversible resistance or capacitance change, or a change in optical properties, analogous to the concentration or the partial pressure to be measured. This reversible change is analogous to the concentration of the sensed vapor or gas. The verifiable sensing limits of the present invention lie considerably under 1 ppm. Since the sensor works reliably in the presence of carrier gas, especially air, it can be used in process control applications, to monitor the workplace, or generally in any environmental area.

In an embodiment of the present invention, the sensor material contains macrocyclic metal complexes, preferably ligands of the crown ether or cryptand type. For example, §-benzo[15]crown-5 or §-benzo-cryptand, for example §-5,6-benzo-4,7,13,16,21,24-hexaoxa-1,10-diazobicyclo-(8,8,8)-hexacosan can be selected as ligands. These ligands are known under the designation §-C2$_B$.2.2. The metal complexes preferably comprise a polymer crown ether or cryptand, which coordinates with a variably charged metal ion, such as a sodium ion $Na^+$, a potassium ion $K^+$, or a magnesium ion $Mg^{++}$, or with a transitional metal ion, such as cobalt $Co^{++}$, nickel $Ni^{++}$ or copper $Cu^{++}$. Polymer structures, which produce stable sensor layers are preferred. Macrocyclic metal complexes with counter ions of variable nucleophiles, such as chloride anions $Cl^-$ or perchlorate anions $ClO_4^-$ are also suited.

In order to promote ionization and to attain selectivity for the sensor, the sensor material may preferably contain protic or aprotic co-substances. These are compounds which are suited for anion or cation solvation and can, therefore, stabilize positively or negatively charged particles. These can be, for example, solid or polyfunctional alcohols; pyrogallol or etherified polyethylene glycols are preferred.

In another embodiment of the present invention, the sensor-active material may be embedded in a matrix, comprising organic or inorganic polymer substances, such as polyvinyl chloride PVC, silicons and collodion. Polymers with active functional groups, suitable for cation and anion solvation, are preferred.

Preferably the sensor-active material is arranged on a carrier, which may be made of materials such as glass, ceramic or plastic. A transparent material, for example, glass or a transparent plastic, preferably a thin polyester film, is preferred for optical measurements.

In general, the electrode arrangement of the sensor comprises a corrosion-resistant metal, preferably gold or platinum, which may be applied to the carrier in any manner known to the art, such as, for example, with photoresist or with collodial solutions.

DETAILED DESCRIPTION OF THE INVENTION

Figure 1:
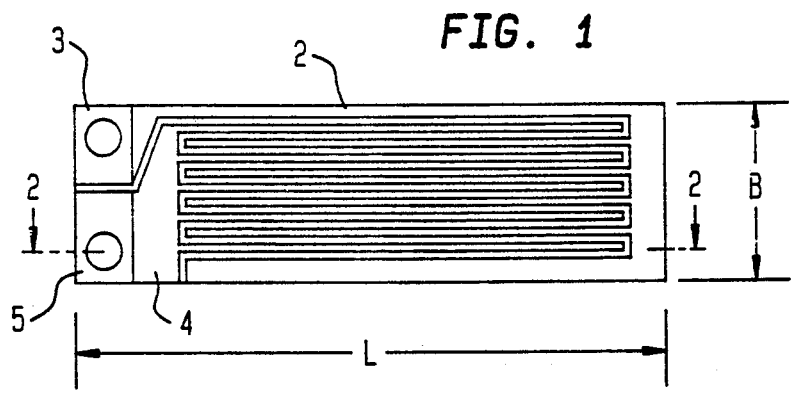
FIG. 1 schematically depicts, in a top view, an embodiment of a sensor, according to the present invention.
Figure 2:
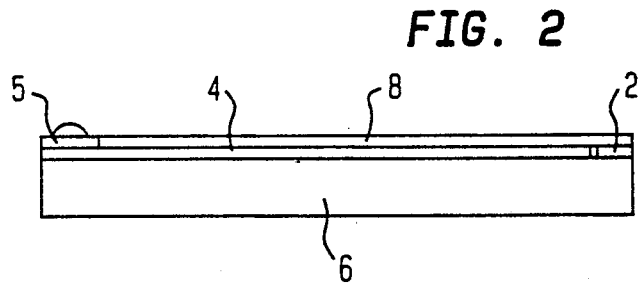
FIG. 2 shows a lateral view of the sensor of FIG. 1.

In the embodiment of a gas sensor according to the present invention, depicted in FIG. 1, two electrodes 2 and 4, in the form of a so-called comb-like structure, are arranged on a substrate, having a length "L" of approximately 40 mm and a width "B" of approximately 8 mm. This substrate is designated 6 in the side view of the sensor shown in FIG. 2. The electrodes 2 and 4, at their extremities 3 or 5, provide for the connection of electric conductors and, for this purpose, they can be provided with additional metal coatings, such as copper. The electrodes 2 and 4 have a width of approximately 100 to 200 $\mu m$ and are arranged at a slight distance, approximately 50 $\mu m$, from each other. A predetermined quantity of a solution comprising the sensor material and a solvent is applied dropwise onto the comb-like structure of both electrodes 2 and 4. Then the solvent is evaporated to form a cohesive sensor layer, 8, of the sensor material having a thickness m at least large enough to avoid the formation of an island. The thickness of the sensor layer, therefore, preferably amounts to at least 50 nm and, in general, does not significantly exceed 2 $\mu m$.

In another embodiment of the gas sensor with a sensor material, according to the present invention a transparent carrier 6 is provided to form a transmitting arrangement. Transparent carrier 6 can comprise glass or transparent plastic, and preferably comprises polyester.

To manufacture the sensor, 52.5 mg crown ether (§-benzo[15]crown-5), in accordance with the following representation, may be dissolved in 25 ml of a tetrahydrofuran/methanol mixture (1:1).

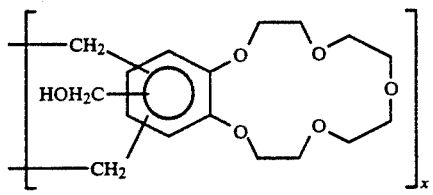

13 mg potassium chloride is added and a somewhat darker solution is obtained. Approximately 100 $\mu l$ of this resulting solution is applied dropwise onto the comb-like structure of the electrodes 2 and 4.

Figure 3:
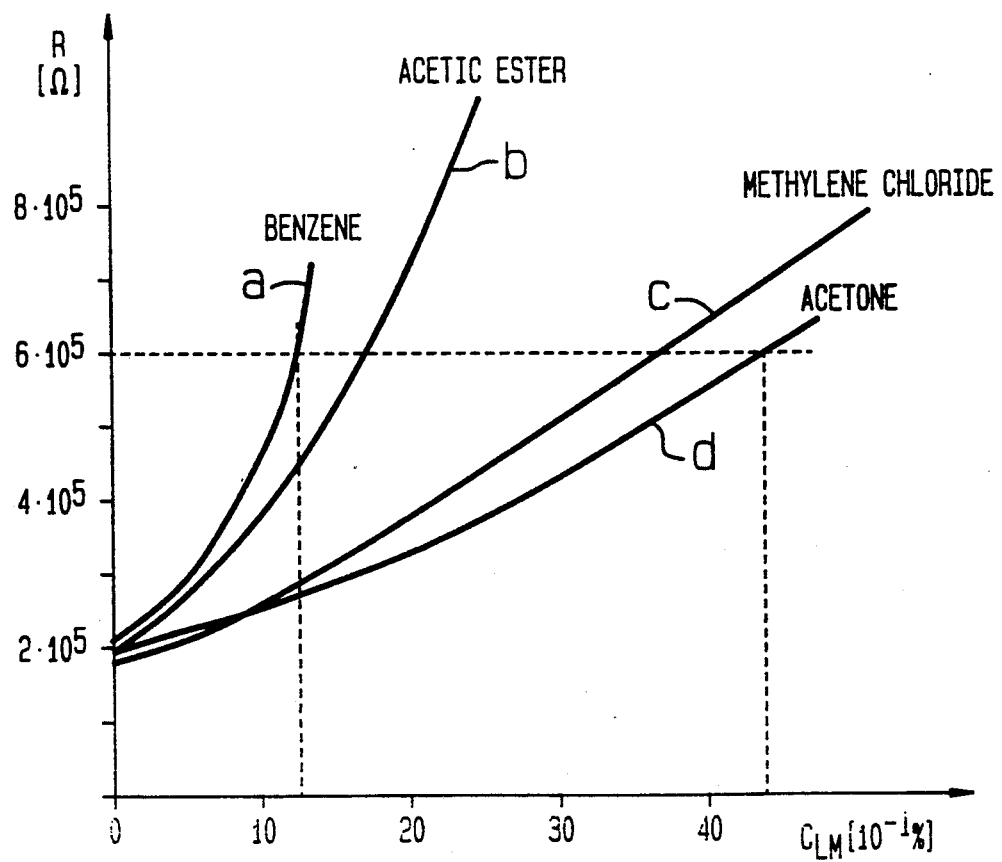
FIG. 3 is a graph plotting the electrical resistance R, in ohms, over the concentration C(LM) of four solvents for a sensor material.

In the diagram of FIG. 3, the electric resistance R in ohms is plotted over the concentration $C_{LM}$ of the solvent in $10^{-1}\%$ for a sensor material comprising an approximately 1 $\mu m$ thick layer of §-benzo 15 crown-5 as ligand and potassium chloride as metal ion. In the curve, (a) benzene, (b) acetic ester, (c) methylene chloride and (d) acetone are provided as solvents. The reaction takes place with an air humidity of 50%. One can see from the diagram that for (d) acetone, as concentration $C_{LM}$ increases from 0% to $45 \times 10^{-1}\%$, resistance increases from $2 \times 10^5$ ohm to $6 \times 10^5$ ohm, as indicated with a dotted line in the diagram. The same resistance value is obtained with a concentration of approximately $12 \times 10^{-1}\%$ benzene in the gas compartment.

In addition to other cations, dually-charged ions, such as magnesium $Mg^{++}$, can be used as a central ion for the macrocyclic ligands. The effect can also be controlled through the counter ion, whereby one varies the nucleophiles of the anion and utilizes the chloride or the perchlorate anion. For this purpose, for example, 21 mg §-benzo 15 crown-5 and 11.7 mg Mg $(ClO_4)_2 \times 6$ $H_2O$ are dissolved in 10 ml of a 6:1 mixture of chloroform and methanol and approximately 100 $\mu l$ of the resulting mixture are applied to the electrode arrangement, according to FIG. 1.

Figure 4:
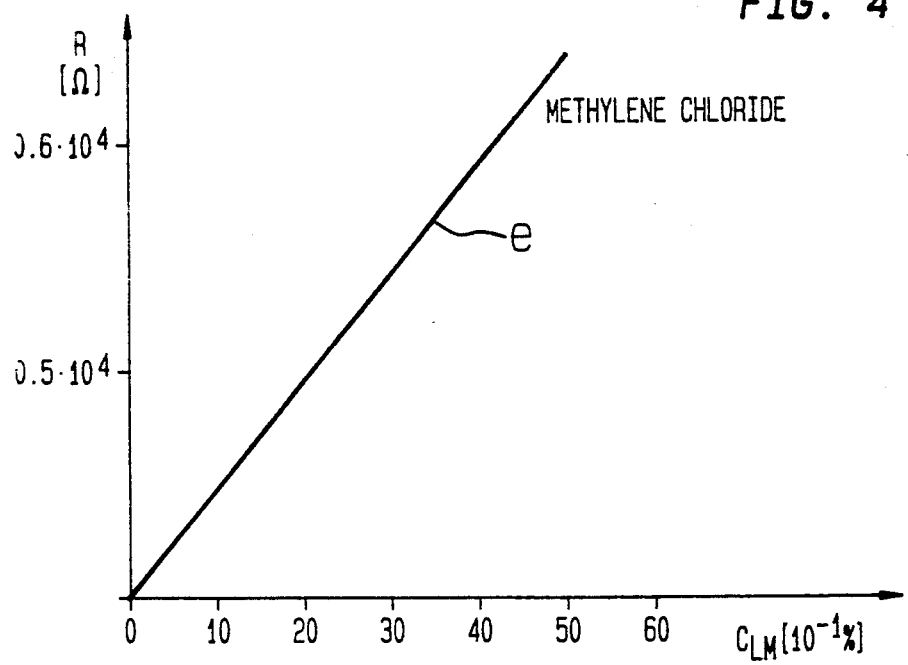
FIG. 4 is a graph plotting the electrical resistance R, in ohms, over the concentration of methylene chloride.

In this embodiment of the sensor, as shown in the diagram of FIG. 4, plotting the electric resistance R in ohm over the concentration $C_{LM}$ of methylene chloride in $10^{-1}\%$, obtains an approximately linear dependency of the resistance R relative to the concentration $C_{LM}$.

The characteristic curve e, shown in the diagram of FIG. 4, results with a methylene chloride concentration in air at approximately 50% air humidity.

Figure 5:
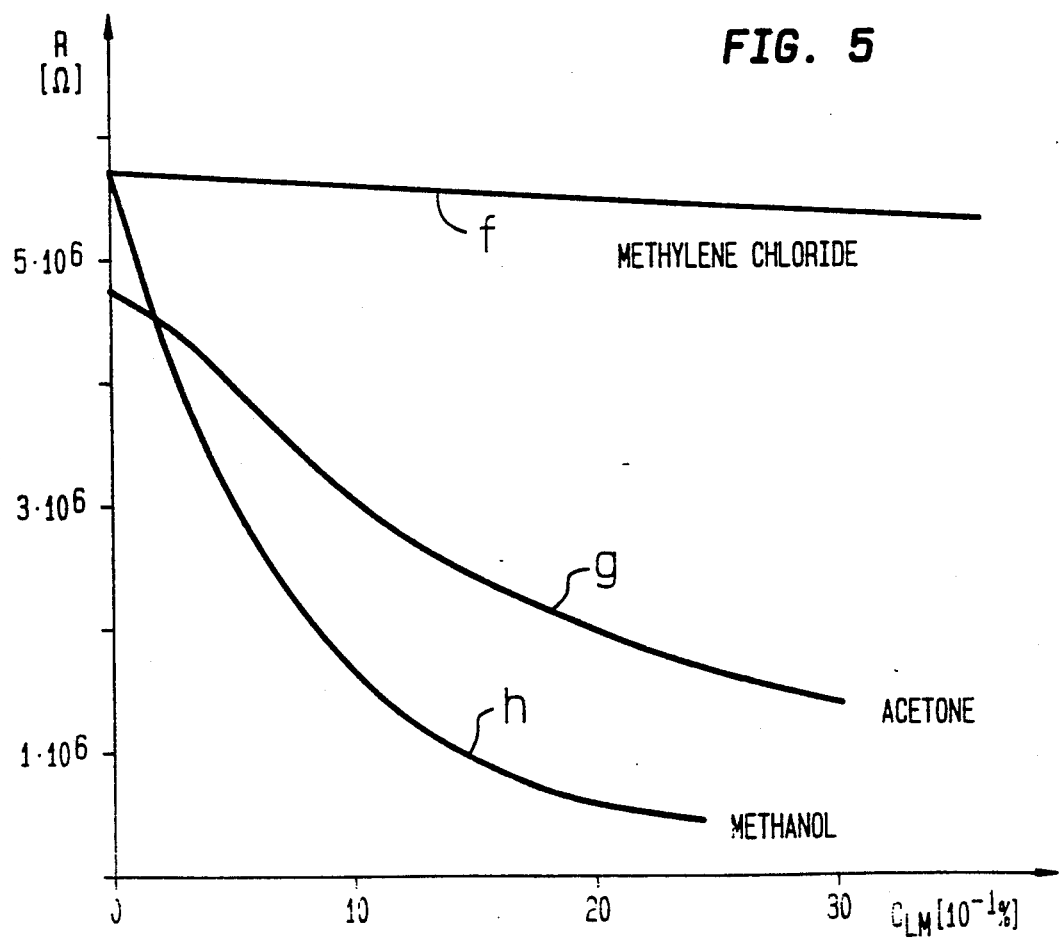
FIG. 5 is a graph plotting the electrical resistance R, in ohms, over the concentration of three solvents at an air humidity of 30%.

If co-solvents are applied when the sensor layer is produced, one can achieve a certain specificity for solvents. If, for example, in the production of the sensor layer made of §-B[15]K-5 dissolved in a mixture of tetrahydrofuran/methanol one adds the protic compound pyrogallol (1:1 weight-% to the ligands §-B[15]K-5), then the resistance of the layer is almost independent of the methylene chloride gas dispersion. Under these conditions in contradistinction to the dependent relationship shown in the diagram of FIG. 3, the resistance, in the case of gas dispersion with acetone and methanol, decreases. This decrease is shown in the diagram of FIG. 5 in which the electric resistance R in ohm is again plotted over the concentration $C_{LM}$ in $10^{-1}$%. The characteristic curves (f) for methylene chloride, (g) for acetone and (h) for methanol are indicated with 30% air humidity.

To produce an oligomer crown ether, the monomeric benzo[15]K-5 may be dissolved in formic acid by adding formaldehyde. The reaction time, the temperature and quantity proportions may be varied to achieve suitable solubilities above the degree of polymerization, for the different applications.

Figure 6:
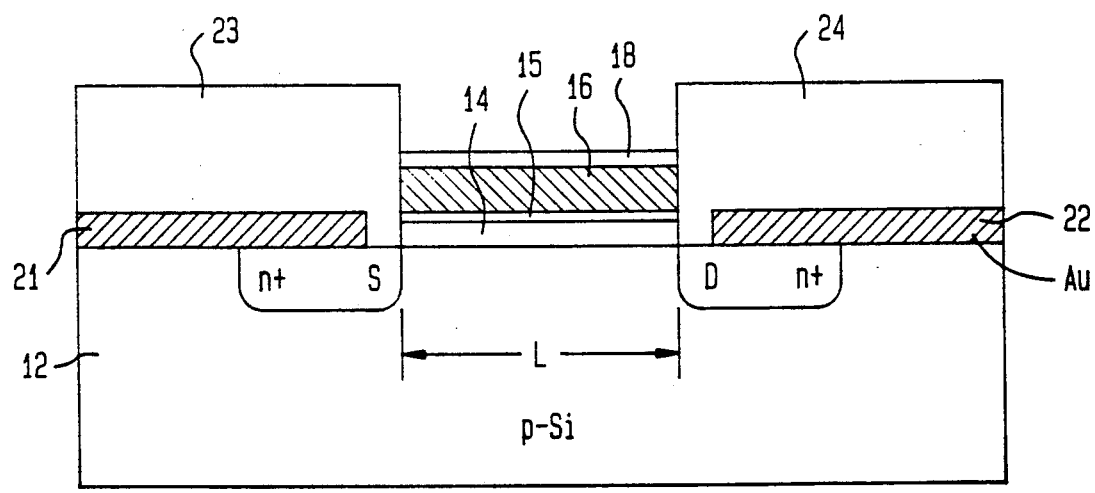
FIG. 6 shows an embodiment of the present invention.

In the embodiment of a gas sensor shown in FIG. 6, a semi-conductor substrate 12, which may comprise p-doped silicon, is provided on its upper flat side with n+-doped surface areas, which serve as a source electrode S or as a drain electrode D. A duct with a length L of, for example, approximately 30 μm is formed between the source electrode S and the drain electrodes D. The surface area of this duct is provided with an insulating layer 14, having a thickness of approximately 70 nm, insulating layer 14 may comprise, silicon dioxide $SiO_2$. This insulating layer 14 is covered by a protective layer 15, having a thickness of approximately 30 nm protective layer 15 may comprise silicon nitride $Si_3N_4$.

Above protective layer 15, a sensor layer 16 having a thickness of, for example, approximately 0.05 to 2 μm is arranged. Sensor layer 16 is covered by a gate electrode 18, which is permeable to gas. The electrode areas of the source electrode S and of the drain electrode D respectively, are partially covered with a metal layer 21 or 22 having a thickness of approximately 1 μmm. Metal layer 21 or 22 may comprise gold Au. The metal layers 21 and 22, and the surface areas of the source electrode S and of the drain electrode D, which border on the duct, are provided with covers 23 and 24, preferably having a thickness of preferably at least a few μm. Covers 23 and 24 may comprise a plastic, preferably polyimide.

The sensor layer 16 at least partially comprises hydrophobic macrocyclic metal complexes with ionic conduction, preferably with ligands of the crown ether or cryptand type, the components and properties of which are clarified in FIGS. 1 to 5.

Gate electrode 18, which is permeable to gas, may comprise a very thin layer of metal, for example, gold (Au), plantinum (Pt) or palladium (Pd), having a thickness of preferably at least 0.01 μm. This thin layer consists of islands, which, on the one hand, form a cohesive layer, yet, have not fully grown together, and thus form apertures which allow gases or vapors to pass through the thin layer. Gate electrode 18 may also comprise a somewhat thicker metal layer having a pattern of bore holes which allow gases or vapors to pass through the layer. The pattern of bore holes may be made by photolithography or by means of a laser beam. The thickness of gate electrode 18 generally does not considerably exceed a few μm. Gate electrode 18 may also comprise parallel strips, or a grid or a net, applied to the sensor layer 16 by vapor-depositing or sputtering. In addition, suspended carbon or metal particles may be applied. Other gate electrodes, generally known under the designation "suspended gate" or "extended gate", are also well suited for use in the present invention.

The sensor of the present inventions provides a simple method for measuring the partial pressure, or the concentration, of gases and vapors, even at room or ambient temperatures. Since it also works reliably in the presence of carrier gas, especially air, it can also be used in process control applications and to monitor the workplace, or generally in the environmental protection area. The sensor obtains a reversible change in the drain-source current analogous to the partial pressure to be measured.

In the embodiment of the present invention, shown in FIG. 6, a specific embodiment of the sensor as a field-effect transistor is depicted, having the sensor layer 16 arranged indirectly on the semiconductor substrate 12. In hybrid technology, wiring systems produced with the laminate method are connected to function groups to form so-called hybrid circuits. In this specific embodiment, as a result of the layer construction, the substrate 12 is spatially separated from sensor layer 16, however, they are connected in an electrically conductive manner.

Besides the specific embodiment of the sensor as a field-effect transistor, the sensor can also be designed as an MOS diode having the sensor layer is likewise arranged between the metal electrode, which is permeable to gas, and the oxide layer.

What is claimed is:

1. Sensor material having electrical or optical properties that change in response to a change in partial pressure of a gas or vapor comprising:
   at least one hydrophobic metal complex having an ion mobility or ionic concentration which changes in response to the change in partial pressure of the gas or vapor.

2. The sensor material of claim 1, wherein the hydrophobic metal complex further comprises macrocyclic metal complexes.

3. The sensor material of claim 2, wherein the macrocyclic metal complexes further comprises crown ether.

4. The sensor material of claim 3, wherein the crown ether further comprises §-benzo 15 crown-5.

5. The sensor material of claim 2, wherein the macrocyclic metal complexes further comprise cryptands.

6. The sensor material of claim 5, wherein the cryptands further comprise §-benzo-cryptands.

7. The sensor material of claim 6, wherein the §-benzo-cryptands further comprise §-$C2_B.2.2$.

8. The sensor material of claim 1 further comprising variably charged metal ions.

9. The sensor material of claim 8, wherein the variably charged metal ions further comprise a metal ion selected from the group consisting of a sodium ion, $Na^+$; a potassium ion, $K^+$; a magnesium ion $Mg^{++}$; a cobalt ion, $Co^{++}$; a nickel ion, $Ni^{++}$; and a copper ion, $Cu^{++}$.

10. The sensor material of claim 2, further comprising variable charged metal ions.

11. The sensor material of claim 10, wherein the variably charged metal ions further comprise another ion selected from the group consisting of a sodium ion, $Na^+$; a potassium ion, $K^+$; a magnesium ion, $Mg^{++}$; a cobalt ion, $Co^{++}$; a nickel ion, $Ni^{++}$; and a copper ion, $Cu^{++}$.

12. The sensor material of claims 1 or 2, further comprising metal complexes having counter ions of variable nucleophiles.

13. The sensor material of claim 10, wherein the counter ions are selected from the group consisting of chloride anions, $Cl^-$ and perchlorate anions, $ClO_4^-$.

14. The sensor material of claim 2, further comprising metal complexes having counter ions of variable nucleophiles.

15. The sensor material of claim 14, wherein the counter ions are selected from the group consisting of chloride anions, $Cl^-$ or perchlorate anions, $ClO_4^-$.

16. The sensor material of claim 1, further comprising at least one protic co-substance.

17. The sensor material of claim 16, wherein the protic co-substance further comprises pyrogallol.

18. The sensor material of claim 1, further comprising at least one aprotic co-substance.

19. The sensor material of claim 18, wherein the aprotic co-substance further comprises etherified polyethylene glycols.

20. The sensor material of claim 1 embedded in a matrix substance.

21. The sensor material of claim 1 arranged on a carrier.

22. The sensor material of claim 21, further comprising a transmitting arrangement with a transparent carrier (6).

23. A field-effect transistor sensor for continuously measuring partial pressure of gases or vapors comprising:
 a semi-conductor substrate having a spaced apart source and drain electrodes;
 an insulating layer on the substrate, between the source and the drain electrode;
 a gas permeable gate electrode spaced apart from the insulating layer; and
 a sensor layer between the gas permeable gate electrode and the insulating layer comprising a sensor material having at least one hydrophobic metal complex having an ion mobility or ionic concentration which changes in response to the change in partial pressure of the gas or vapor.

24. The sensor of claim 23, further comprising substituted phthalide.

25. The sensor of claim 24, wherein the substituted phthalide further comprises a 3-(N-methyl-3-indolyl)-6-dimethylaminophthalide.

26. The sensor of claim 24, wherein the substituted phthalide further comprises a 3,3-diphenylphthalide.

27. The sensor of claim 26, wherein the 3,3-diphenylphthalide further comprises 3,3-bis(p-dimethylaminophenyl)-6-dimethylaminophthalide.

28. The sensor of claim 26, wherein the 3,3-diphenylphthalide further comprises 3-(p-dimethylaminophenyl)-3-(p-methoxyphenyl)-6-dimethylaminophthalide.

29. The sensor of claim 23, further comprising phenolic acids.

30. The sensor of claim 29, wherein the phenolic acids further comprise 2.2-bis(4-hydroxyphenyl)-propane.

31. The sensor of claim 26, wherein the phenolic acids further comprise hydroxy-(phenyl)-bis(p-hydroxyphenyl)-methane.

32. The sensor of claim 23, having a hybrid type of construction.

* * * * *